United States Patent
Matsumoto et al.

(10) Patent No.: US 6,462,246 B2
(45) Date of Patent: Oct. 8, 2002

(54) METHOD OF PREPARING ALKENYL-SUBSTITUTED AROMATIC HYDROCARBON

(75) Inventors: Takaya Matsumoto; Shinji Nishikawa; Hajime Yoshida, all of Yokohama (JP)

(73) Assignee: Nippon Mitsubishi Oil Corporation, Tokyo (JP)

( * ) Notice: Subject to any disclaimer, the term of this patent is extended or adjusted under 35 U.S.C. 154(b) by 0 days.

(21) Appl. No.: 09/819,904

(22) Filed: Mar. 29, 2001

(65) Prior Publication Data

US 2001/0037044 A1 Nov. 1, 2001

(30) Foreign Application Priority Data

Mar. 30, 2000 (JP) .................................. 2000-094932

(51) Int. Cl.⁷ .......................... C07C 15/46; C07C 5/09; C07C 2/66
(52) U.S. Cl. ...................... 585/438; 585/435; 585/436; 585/437; 585/457
(58) Field of Search ................... 585/435, 436, 585/437, 438, 457

(56) References Cited

U.S. PATENT DOCUMENTS 3,775,511 A 11/1973 Shue .......................... 260/669
3,848,010 A 11/1974 Intille ......................... 260/668

FOREIGN PATENT DOCUMENTS

JP 51-14496 5/1976

OTHER PUBLICATIONS

Fujiwara et al.; "Aromatic Substitution of Olefins. VI. Arylation of Olefins with Palladium (II) Acetate"; Journal of the American Chemistry Society; vol. 91, No. 25; Dec. 3, 1969; pp. 7166–7169.

Primary Examiner—Thuan D. Dang
(74) Attorney, Agent, or Firm—Foley & Lardner

(57) ABSTRACT

A method of preparing an alkenyl-substituted aromatic hydrocarbon, which comprises alkenylating an aromatic hydrocarbon with an olefin using β-diketone together with a rhodium complex catalyst in the presence of oxygen.

23 Claims, No Drawings

METHOD OF PREPARING ALKENYL-SUBSTITUTED AROMATIC HYDROCARBON

BACKGROUND OF THE INVENTION

1. Field of the invention

The present invention relates to a method of directly synthesizing an alkenyl-substituted aromatic hydrocarbon from an aromatic hydrocarbon and an olefin in one step.

More specifically, the present invention relates to a method of preparing styrene by alkenylating benzene with ethylene.

2. Description of the Related Art

Styrene has hitherto been prepared by a two-step process, that is, alkylation of benzene due to ethylene and dehydrogenation of ethylbenzene obtained therefrom.

As a one-step synthesis process of synthesizing styrene directly from ethylene and benzene, a liquid phase reaction using palladium acetate has been reported by FUJIWARA (J. Am. Chem. Soc. O, 1969, 1910, 7166). In this process, the use of copper acetate or silver acetate as a redox agent makes it possible to conduct a catalytic partial oxidation reaction due to oxygen, but the reaction rate and the selectivity of styrene are low.

Although an improvement in stability of the catalyst was made by adding carboxylic acid amide (Examined Patent Publication (Kokoku) No. 51-14496), vinyl acetate, as a by-product, formed from acetic acid used as an essential solvent and ethylene cannot be inhibited and the selectivity of styrene is not sufficient. A one-step process of synthesizing styrene using a transition metal of the Group VIII (e.g. iron, cobalt, nickel, ruthenium, rhodium, palladium, osmium, iridium, platinum, etc.) is disclosed in U.S. Pat. No. 3,848,010. However, in the one-step process of synthesizing styrene, the presence of carboxylic acid such as acetic acid is indispensable and a carboxylic acid ester such as vinyl acetate, as a by-product, can not be avoided by the prior art. Therefore, it is still difficult to selectively produce only styrene.

A method of selectively preparing styrene using rhodium in the absence of carboxylic acid has been suggested by one of the present inventors (U.S. patent Ser. No. 09/277,327). However, according to any of the one-step techniques of synthesizing styrene described above, a redox agent such as copper-containing compound is indispensable to reoxidize the transition metal of the Group VIII reduced by the reaction in order to enable the transition metal of the Group VIII to serve as the catalyst. The redox agent, which is reduced by oxidizing the transition metal of the Group VIII during the reaction, itself can be reoxidized by air or oxygen. That is, according to the prior art, the coexistence of the transition metal of the Group VIII, which serves as the catalyst, redox agent and oxygen (air) was an essential condition in order to catalytically carry out this reaction.

Although the method of conducting the reaction between an aromatic hydrocarbon and styrene using palladium acetate and using only oxygen as an oxidizing agent has been known (U.S. Pat. No. 3,775,511), a principal product is acetophenone and the selectivity of stilbene as an alkenylated product is low.

As used herein, the term "selectively prepare" or "selectively produce" means that a desired aromatic hydrocarbon is prepared or produced in a relatively higher proportion than that of the other products. Similarly, the term "high selectivity" means that a target alkenyl-substituted aromatic hydrocarbon is produced in a higher proportion than that of the other reaction products (undesirable products). Similarly, the term "mainly include" means that the amount of the product is significantly larger than that of the other products.

The present invention makes it possible to efficiently prepare a predetermined alkenyl-substituted aromatic hydrocarbon, which has never before been selectively obtained by a conventional method, efficiently by using a specific catalyst and adding β-diketone. This method may preferably be carried out also in the absence of a redox agent.

The aromatic hydrocarbon obtained by the reaction can be optionally separated by a conventional method such as distillation to give a final product.

BRIEF SUMMARY OF THE INVENTION

An object of the present invention is to provide a novel method of synthesizing an alkenyl-substituted aromatic hydrocarbon by alkenylation of an aromatic hydrocarbon due to an olefin at a high selectivity. Particularly, the present invention relates to a method of preparing an alkenyl-substituted aromatic hydrocarbon, which comprises using a rhodium complex as a catalyst and adding β-diketone in the case where an aromatic hydrocarbon is alkenylated with an olefin in the presence of oxygen without necessarily requiring a redox agent such as copper-containing compound or silver-containing compound. An example of a useful reaction includes a reaction of preparing styrene by alkenylating benzene with ethylene. Styrene is a compound which is useful as a raw material of polystyrene.

The present inventors have intensively studied methods of preparing an alkenyl-substituted aromatic hydrocarbon in the presence of oxygen. As a result, they have found a method of selectively alkenylating an aromatic hydrocarbon by using a rhodium complex as a catalyst and adding β-diketone.

This invention relates to a method of preparing an alkenyl-substituted aromatic hydrocarbon, which comprises alkenylating an aromatic hydrocarbon with an olefin using β-diketone together with a rhodium complex catalyst in the presence of oxygen and in the absence of a redox agent.

This invention relates to the method of preparing an alkenyl-substituted aromatic hydrocarbon, wherein said olefin is a substituted or non-substituted olefin having 2 to 20 carbon atoms (in which a substituent may be straight-chain or branched and also may contain a heteroatom or heteroatoms) and said aromatic hydrocarbon is a monocyclic or polycyclic aromatic hydrocarbon having 6 to 20 carbon atoms (said aromatic hydrocarbon may have a substituent and the substituent may contain a heteroatom or heteroatoms).

This invention also relates to the method of preparing an alkenyl-substituted aromatic hydrocarbon, wherein said β-diketone is β-diketone represented by the following scheme (1).

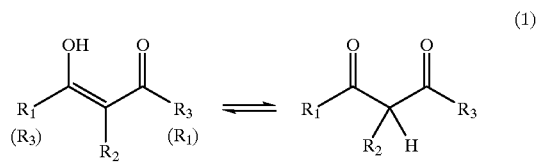

(1)

(provided that $R_1$ to $R_3$ respectively represent an arbitrary substituent and may be the same).

This invention also relates to the method of preparing an alkenyl-substituted aromatic hydrocarbon, wherein said β-diketone is 2,4-pentanedione(acetylacetone) or 2,2,6,6-tetramethyl-3,5-heptanedione.

This invention further relates to the method of preparing an alkenyl-substituted aromatic hydrocarbon, wherein said rhodium complex is a complex in the formal oxidation state of Rh (I).

This invention further relates to the method of preparing an alkenyl-substituted aromatic hydrocarbon, wherein said rhodium complex is a complex having at least one rhodium atom and at least one β-diketonato ligand.

This invention specifically relates to the method of preparing an alkenyl-substituted aromatic hydrocarbon, wherein said rhodium complex is any one selected from dicarbonylacetylacetonatorhodium (I), acetylacetonatobis (ethylene)rhodium (I), chloro(1,5-cyclooctadiene)rhodium (I) dimer, chlorotris(triphenylphosphine)rhodium (I), and norbornadiene[1,4-bis(diphenylphosphino)butane]rhodium (I) tetrafluoroborate.

This invention more specifically relates to the method of preparing an alkenyl-substituted aromatic hydrocarbon, wherein said olefin is ethylene and said aromatic hydrocarbon is benzene.

DETAILED DESCRIPTION OF THE INVENTION

The present invention will be described in detail below.

The formal oxidation state of Rh (I) used in the present invention means that a starting substance of a catalyst is rhodium (I). Similarly, the formal oxidation state of Rh (III) means that a starting substance of a catalyst is rhodium (III).

The aromatic hydrocarbon used in the present invention is a cyclic compound wherein a π electron orbital is delocalized, and any monocyclic and polycyclic compound can be used. Specifically, it is an aromatic hydrocarbon having 6 to 20 carbon atoms, and preferably 6 to 12 carbon atoms. At least one atom of the aromatic ring is hydrogen which is covalently bonded with the atom. Such an aromatic hydrocarbon can contain a substituent.

The substituent may be straight-chain, branched, or cyclic. Examples of the substituent include, but are not limited to, an alkyl group, a cycloalkyl group, an aryl group, an alkaryl group, an aralkyl group and the like. Examples of the alkyl group include, but are not limited to, a methyl group, an ethyl group, an isopropyl group, a n-propyl group, an isobutyl group, a n-butyl group, a sec-butyl group, a tert-butyl group and the like. Examples of the cycloalkyl group include, but are not limited to, a cyclopropyl group, a cyclobutyl group, a cyclopentyl group, a cyclohexyl group and the like.

Examples of the aryl group include, but are not limited to, a phenyl group, a naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like.

The aromatic hydrocarbon and substituent of the aromatic hydrocarbon can further contain one or more than one non-hydrocarbon substituents having one or more atoms other than hydrogen and carbon. Examples of the non-hydrocarbon substituent include, but are not limited to, a halogen atom(s) (—F, —Cl, —Br, —I), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide groups (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide group (—CF$_3$) and the like. Preferably, the aromatic hydrocarbon and substituent of the aromatic hydrocarbon are those which do not poison a rhodium catalyst described below and do not induce an undesirable secondary reaction.

Specific examples of the monocyclic aromatic include, but are not limited to, benzene, methylbenzene (toluene), 1,2-dimethylbenzene (o-xylene), 1,3-dimethylbenzene (m-xylene), 1,4-dimethylbenzene (p-xylene), 1,3,5-trimethylbenzene (mesitylene), 1,2,3-trimethylbenzene, 1,2,4-trimethylbenzene, tetramethylbenzene, pentamethylbenzene, ethylbenzene, n-propylbenzene, isopropylbenzene (cumene), 1-isopropyl-4-methylbenzene (p-cymene), n-butylbenzene, 2-butylbenzene, isobutylbenzene, tert-butylbenzene, n-pentylbenzene, cyclopentylbenzene, neopentylbenzene, cyclohexylbenzene, 1-cyclohexyl-4-methylbenzene, cyclooctylbenzene and the like.

Specific examples of the polycyclic aromatic hydrocarbon include, but are not limited to, biphenyl, biphenylene, terphenyl, naphthalene, azulene, anthracene, phenanthrene, triphenylene, pyrene, 1-methylnaphthalene, 2-methylnaphthalene, 1-ethylnaphthalene, 2-ethylnaphthalene, 2,21-dimethylbiphenyl, diphenylethane, 1,2-diphenylethane, 1,8-diphenyloctane and the like.

Specific examples of the aromatic hydrocarbon containing a heteroatom include, but are not limited to, methoxybenzene (anisole), ethoxybenzene, nitrobenzene, methyl benzoate, ethyl benzoate, isobutyl benzoate, diphenyl ether, cyclohexyl phenyl ether, benzonitrile, phenyl acetate, phenyl hexanoate, tolyl acetate, phenol, benzaldehyde, acetophenone, chlorobenzene, 2-chloroxylene, bromobenzene, trichlorobenzene, 1,4-dichlorobenzene, 1,2-dibromonaphthalene and the like.

Specific example of more preferred aromatic hydrocarbon is benzene.

The olefin used in the present invention is a compound having at least one carbon-carbon double bond, and any straight-chain, branched and cyclic compound can be used. Specifically, it is an olefin having 2 to 20 carbon atoms, and preferably 2 to 12 carbon atoms. Such an olefin can contain a substituent.

The substituent may be straight-chain, branched, cyclic, saturated, or unsaturated. Examples of the substituent include, but are not limited to, alkyl group, cycloalkyl group, aryl group, alkaryl group, aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like.

Examples of the aryl group include, but are not limited to, phenyl group, naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like.

Examples of the aralkyl group include, but are not limited to, phenylmethyl group (benzyl group), phenylethyl group (phenethyl group), triphenylmethyl group (trityl group) and the like. Examples of the unsaturated hydrocarbon substituent include, but are not limited to, vinyl group, allyl group and the like.

The olefin and substituent of the olefin can further contain one or more than one non-hydrocarbon substituent having one or more atoms other than hydrogen and carbon. Examples of the non-hydrocarbon substituent include, but are not limited to, a halogen atom(s) (—F, —Cl, —Br, —I), hydroxyl group (—OH), alkoxy groups (—OR), carboxyl group (—COOH), ester groups (—COOR), aldehyde group (—CHO), acyl groups (—C(=O)R), amide group (—C(=O)NH$_2$), substituted amide groups (—C(=O)NHR), —C(=O)NR$_2$), amino group (—NH$_2$), substituted amino groups (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like. Preferably, the olefin and substituent of the olefin are those which do not poison a rhodium catalyst described below and do not induce an undesirable secondary reaction.

Specific examples of the straight-chain monoolefin include, but are not limited to, ethylene, propylene, 1-butene, 2-butene, straight-chain pentene (e.g. 1-pentene, 2-pentene, etc.), straight-chain hexene (e.g. 1-hexene, 2-hexene, 3-hexene, etc.), straight-chain heptene (e.g. 1-heptene, etc.), straight-chain octene (e.g. 1-octene, etc.), straight-chain nonene (e.g. 1-nonene, etc.), straight-chain decene (e.g. 1-decene, etc.), straight-chain dodecene (e.g. 1-dodecene, etc.), and straight-chain eicosene (e.g. 1-eicosene, etc.).

Specific examples of the branched monoolefin include, but are not limited to, isobutene (2-methylpropylene), 2-methyl-1-butene, 3-methyl-1-butene, 2,3,3-trimethyl-1-butene, 2-methyl-2-butene and the like.

Specific examples of the cyclic monoolefin include, but are not limited to, cyclopentene, methylcyclopentene, cyclohexene, 1-methylcyclohexene, 3-methylcyclohexene, 1,2-dimethylcyclohexene, cyclooctene and the like.

Specific examples of the polyolefin include, but are not limited to, 1,2-butyadiene (methylallene), 1,3-butadiene (bivinyl), 1,3-pentadiene, 1,5-heptadiene, divinylbenzene, vinylcyclohexene, allylcyclohexene and the like.

Specific examples of the olefin containing a heteroatom include, but are not limited to, vinyl chloride, vinyl fluoride, vinylidene chloride, allyl bromide, chlorostyrene, trichloroethylene, acrylic acid, crotonic acid, maleic acid, methyl maleate, p-vinylbenzoic acid, vinyl acetate, allyl propionate, propenyl acetate, ethylidene diacetate, methyl acrylate, methyl methacrylate and the like.

A specific example of a more preferred olefin is ethylene.

β-diketone used in the present invention is an organic compound having two keto groups at intervals of a carbon atom in a molecule, and exists as an equilibrium mixture of enol type and keto type tautomers as shown in the scheme (2) described below. Such β-diketone can contain a substituent at the positions of R$_1$ and R$_3$, and can contain a hydrogen atom or substituent at the position of R$_2$. R$_1$, R$_2$ and R$_3$ may be the same or different with each other. The substituent may be straight-chain, branched, cyclic, saturated, or unsaturated.

Examples of the substituent include, but are not limited to, an alkyl group, a cycloalkyl group, an aryl group, an alkaryl group, an aralkyl group and the like. Examples of the alkyl group include, but are not limited to, methyl group, ethyl group, isopropyl group, n-propyl group, isobutyl group, n-butyl group, sec-butyl group, tert-butyl group and the like. Examples of the cycloalkyl group include, but are not limited to, cyclopropyl group, cyclobutyl group, cyclopentyl group, cyclohexyl group and the like.

Examples of the aryl group include, but are not limited to, phenyl group, naphthyl group and the like. Examples of the alkaryl group include, but are not limited to, 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylxylyl group (mesityl group) and the like. Examples of the aralkyl group include, but are not limited to, phenylmethyl group (benzyl group), phenylethyl group (phenethyl group), triphenylmethyl group (trityl group) and the like. Examples of the unsaturated hydrocarbon substituent include, but are not limited to, vinyl group, allyl group and the like.

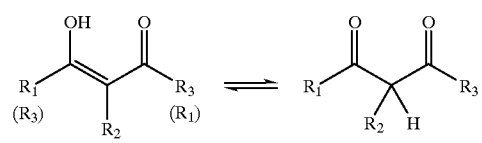

(2)

(provided that R$_1$ to R$_3$ respectively represent an arbitrary substituent and may be the same)

A β-diketone and a substituent of β-diketone can further contain one or more than one non-hydrocarbon substituent having one or more atoms other than hydrogen and carbon. Examples of the non-hydrocarbon substituent include, but are not limited to, a halogen atom(s) (—F, —Cl, —Br, —I), hydroxyl group (—OH), alkoxy groups (—OR), carboxyl group (—COOH), ester groups (—COOR), aldehyde group (—CHO), acyl group (—C(=O)R), amide group (—C(=O)NH$_2$), substituted amide groups (—C(=O)NHR), —C(=O)NR$_2$), amino group (—NH$_2$), substituted amino group (—NHR, —NR$_2$), nitro group (—NO$_2$), nitroso group (—NO), cyano group (—CN), cyanate group (—OCN), isocyanate group (—NCO), thiocyanate group (—SCN), isothiocyanate group (—NCS), thiol group (—SH), thioether groups (—SR), sulfo group (—SO$_3$H), alkyl halide groups (—CF$_3$) and the like.

Specific examples of β-diketone containing a subsequent include, but are not limited to, 2,4-pentanedione (acetylacetone), 3-methyl-2,4-pentadione, 2,4-hexanedione, 2,2,6,6-tetramethyl-3,5-heptanedione, and 1,3-diphenyl-1,3-propanedione and the like.

Specific examples of β-diketone containing a heteroatom include, but are not limited to, 1,1,1-trifluoro-2,4-pentanedione, 1,1,1,5,5,5-hexafluoro-2,4-pentanedione (1,1,1,5,5,5-hexafluoroacetylacetone), 1,1,1-trifluoro-2,4-hexanedione, 1,1,1,2,2-pentafluoro-3,5-heptanedione, 1,1,1,2,2,6,6,7,7,7-decafluoro-3,5-heptanedione and the like.

Specific examples of more preferred β-diketone are 2,4-pentadione (acetylacetone) and 2,2,6,6-tetramethyl-3,5-heptanedione.

The catalyst in the present invention is a rhodium complex. Like the Examples described below, a complex in the formal oxidation state of Rh (I) is more preferable as compared with a complex in the formal oxidation state of Rh (III). A rhodium complex containing at least one β-diketonato ligand is effective as the catalyst.

The β-diketonato ligand is a ligand obtained by proton dissociation of an enol tautomer of β-diketone or a ligand obtained by proton dissociation of an keto tautomer of β-diketone.

Specific examples of more preferred catalyst are dicarbonylacetylacetonato rhodium (I), acetylacetonatobis (ethylene) rhodium (I), chloro(1,5-cyclooctadiene) rhodium (I) dimer, chlorotris(triphenylphosphine) rhodium (I), and norbornadiene[1,4-bis(diphenylphosphino)butane]rhodium (I) tetrafluoroborate. These catalysts are commercially available.

In the present invention, the term "redox agent" refers to a redox agent which has a capability of oxidizing a reduced catalyst (rhodium catalyst), a reduced substance of the redox agent being capable of being oxidized with oxygen or air. That is, the redox agent oxidizes the rhodium complex reduced again by the reaction, whereby the redox agent itself is reduced. The reduced redox agent can obtain again a capability of oxidizing the reduced rhodium complex again by being oxidized again with air or oxygen, and serves as the redox agent. Specific examples thereof include copper (II) acetate, copper (II) oxide, copper (II) chloride, silver (I) acetate, heteropolyacid ($H_{3+n}PMo_{12-n}V_nO_{40}$ (n=1-6) and the like.

The present invention provides a method of preparing an alkenyl-substituted aromatic hydrocarbon, which comprises alkenylating an aromatic hydrocarbon with an olefin using β-diketone together with a rhodium complex catalyst in the presence of oxygen. The present method may be carried out using the redox agent described above, however, if it is used, it may possibility cause a side reaction and thus it needs a further process to remove it after the reaction. Accordingly, it is preferable not to use the redox agent.

In the case where the aromatic hydrocarbon is liquid or the aromatic hydrocarbon and olefin are liquids in the present invention, the reaction medium may substantially be an aromatic hydrocarbon, or an aromatic hydrocarbon and an olefin. Therefore, solvents are not necessarily required, but may also be added. In the case where the aromatic hydrocarbon is solid, a solvent is required for dissolving the catalyst. The reaction can be conducted by using, as the solvent, a saturated hydrocarbon (e.g. n-heptane, 2,2,5,5-tetramethylhexane, etc.) or ether (e.g. ethylene glycol diethyl ether, etc.) which is inert to the reaction, or an aromatic hydrocarbon (e.g. 1,3,5-tri-tert-butylbenzene, etc.) which is inert to the reaction and is coated with a substituent causing large steric hindrance.

The reaction is conducted by using an apparatus suited for the selected olefin compound and aromatic compound. When the aromatic compound is liquid at the reaction temperature and the olefin compound is gas at the reaction temperature (e.g. benzene/ethylene), a pressure reaction vessel is most suited. When the aromatic hydrocarbon and olefin are liquids at the reaction temperature, a heatable reaction vessel or a reflux apparatus are most suited.

The reaction can be conducted by any batch-wise, semibatch-wise and continuous method. The reaction is conducted by the batch-wise manner in the laboratory because of its simplicity, but it can be conducted in a continuous manner from an industrial point of view.

Each amount of the aromatic compound, olefin compound, rhodium complex catalyst and β-diketone can be selected appropriately to optimize reaction parameters, for example, catalyst turn over frequency, selectivity, and yield.

The molar ratio of the aromatic hydrocarbon as the reaction raw material to the rhodium complex as the catalyst is not specifically limited as far as the reaction proceeds, but is substantially within a range from 100000:1 to 10:1, and preferably from 50000:1 to 100:1.

The molar ratio of the aromatic hydrocarbon to the olefin compound varies widely. A suitable molar ratio of the aromatic hydrocarbon to the olefin compound is within a range from 0.1:1 to 1000:1. Since the aromatic compound can often serve as a reaction agent and a reaction medium, the aromatic hydrocarbon and the olefin compound are preferably used in a molar ratio of 1:1 or more (i.e. stoichiometrically excess aromatic compound).

The molar ratio of β-diketone to the rhodium complex catalyst varies widely. Usually, a molar ratio of 1 or more is employed to make the catalytic effect advantageous. Preferably, the molar ratio is 50:1 or more.

In the case where the method of the present invention is carried out, the reaction temperature is within a range from normal temperature to 300° C., and is preferably from 120 to 220° C.

The reaction pressure is within a range from atmospheric pressure to 30 MPa, and preferably from 0.5 to 5 MPa.

The reaction is conducted for a time enough to completely convert the olefin compound as the starting substance. However, the amount of the product increases with proceeding of the reaction, a problem such as undesirable secondary reaction, e.g. polyarylation arises. Therefore, the reaction is preferably terminated at a point of time where conversion of the olefin compound as the starting substance has not been completed, in order to optimize the yield of the desired product. The optimum time depends on properties of reaction materials, and selected operation conditions such as temperature, molar ratio of reaction materials and the like.

EXAMPLES

The following Examples further illustrate the present invention in detail, but the present invention is not limited by these Examples.

Example 1

A Rh(acac)(CO)$_2$/benzene/acetic acid solution having an Rh concentration of 1 mM and a benzene concentration of 10.6 M was prepared from dicarbonylacetylacetonato rhodium(I) (hereinafter referred to as Rh(acac)(CO)$_2$), benzene and acetic acid. 3 ml of the resulting solution, a stir bar coated with Teflon, and 0.2 g of acetylacetone were introduced in a glass inner cylinder, which was then introduced in a stainless steel autoclave. After the atmosphere in the autoclave was purged by nitrogen, ethylene was injected up to 1.55 MPa at room temperature and oxygen was injected up to 2.10 MPa, followed by heating with stirring at 180° C. for 20 minutes. After cooling, the liquid phase was analyzed by gas chromatography. The results are shown in Table 1.

Comparative Example 1

The reaction was conducted by the very same operation as in Example 1, except that 27 mg of copper acetate (hereinafter referred to as Cu(OAc)$_2$) was added in place of acetylacetone. The results are shown in Table 1. Copper acetate serves as an oxidation auxiliary (the same rule applied correspondingly to the following).

Comparative Example 2

The reaction was conducted by the very same operation as in Example 1, except that acetylacetone was not added. The results are shown in Table 1.

Example 2

The reaction was conducted by the very same operation as in Example 1, except that norbornadiene[1,4-bis (diphenylphosphino)butane]rhodium (I) tetrafluoroborate (hereinafter referred to as Rh(NBD)(DPPB)BF$_4$) was used in place of Rh(acac)(CO)$_2$. The results are shown in Table 1.

Comparative Example 3

Synthesis Reaction of Butylbenzene

The reaction was conducted by the very same operation as in Example 2, except that 27 mg of Cu(OAc)$_2$) was added in place of acetylacetone. The results are shown in Table 1.

Comparative Example 4

The reaction was conducted by the very same operation as in Example 2, except that acetylacetone was not added. The results are shown in Table 1.

Comparative Example 5

The reaction was conducted by the very same operation as in Example 1, except that palladium acetate (hereinafter referred to as Pd(OAc)$_2$) was used in place of Rh(acac)(CO)$_2$. The results are shown in Table 1.

Comparative Example 6

The reaction was conducted by the very same operation as in Comparative Example 5, except that 27 mg of Cu(OAc)2) was added in place of acetylacetone. The results are shown in Table 1.

Example 3

The reaction was conducted by the very same operation as in Example 1, except that acetylacetonatobis(ethylene)rhodium (I) (hereinafter referred to as Rh(acac)(ethylene)$_2$) was used in place of Rh(acac)(CO)$_2$. The results are shown in Table 1.

Example 4

The reaction was conducted by the very same operation as in Example 1, except that chloro(1,5-cyclooctadiene)rhodium (I) dimer (hereinafter referred to as [Rh(COD)Cl]$_2$) was used in place of Rh(acac)(CO)$_2$. The results are shown in Table 1.

Example 5

The reaction was conducted by the very same operation as in Example 1, except that chlorotris(triphenylphosphine)rhodium (I) dimer (hereinafter referred to as RhCl(PPh$_3$)$_3$) was used in place of Rh(acac)(CO)$_2$. The results are shown in Table 1.

Example 6

The reaction was conducted by the very same operation as in Example 1, except that dichloro(pentamethylcyclopentadienyl)rhodium (III) dimer (hereinafter referred to as [Rh(Cp*)Cl$_2$]$_2$ was used in place of Rh(acac)(CO)$_2$. The results are shown in Table 1.

Example 7

The reaction was conducted by the very same operation as in Example 1, except that bis(2-phenylpyridine)rhodium (III) acetate (hereinafter referred to as Rh(ppy)$_2$(OAc)) was used in place of Rh(acac)(CO)$_2$. The results are shown in Table 1.

Example 8

The reaction was conducted by the very same operation as in Example 1, except that 2,2,6,6-tetramethyl-3,5-heptanedione was used in place of acetylacetone. The results are shown in Table 1.

Example 9

The reaction was conducted by the very same operation as in Example 1, except that 1,1,1,5,5,5-hexafluoro-2,4-pentanedione was used in place of acetylacetone. The results are shown in Table 1.

Example 10

The reaction was conducted by the very same operation as in Example 1, except that tert-butyl acetoacetate was used in place of acetylacetone. The results are shown in Table 1.

As is apparent from the results of Examples 1 to 7 in Table 1, formation of styrene is recognized in the absence of a redox agent by using the rhodium complex as the catalyst and adding acetylacetone. It has also been found that, regardless of the reaction in acetic acid, styrene can be formed selectively without forming any vinyl acetate as a by-product. When using copper acetate as the redox agent (Comparative Examples 1 and 3), formation of vinyl acetate can be recognized.

As is apparent from in Comparative Examples 2 and 4, it is difficult to conduct the oxidation reaction using only oxygen and, therefore, formation of styrene is hardly recognized or a trace amount of styrene is formed. With regard to palladium, the selectivity of styrene is improved by the addition of acetylacetone in the absence of the redox agent, but formation of vinyl acetate as a by-product can not be avoided (Comparative Examples 5 and 6). As the rhodium complex, a complex in the formal oxidation state of rhodium (I) shows good results as compared with a complex in the formal oxidation state of rhodium (III). In the study of β-diketone, acetylacetone and 2,2,6,6-tetramethyl-3,5-heptanedione show good results.

In this table, mM (millimolar) is a molar concentration of the product in the reaction solution. TOF (turn over frequency) was defined as follows. TOF=[(mole number of product)/(mole number of catalyst)]/reaction time (second)

TABLE 1

Results of alkenylation reaction between ethylene and benzene

| | Catalyst | Formal oxidation state | Oxidizing agent | β-diketone | Molar concentration of product (mM) | | TOF ($\times 10^{-4} s^{-1}$) | |
|---|---|---|---|---|---|---|---|---|
| | | | | | Vinyl acetate | Styrene | Vinyl acetate | Styrene |
| Example 1 | Rh(acac)(CO)$_2$ | Rh(I) | O$_2$ | acacH | 0.0 | 22.5 | 0.0 | 187.5 |
| Comp. Example 1 | Rh(acac)(CO)$_2$ | Rh(I) | Cu(OAc)$_2$/O$_2$ | — | 10.0 | 29.8 | 83.2 | 248.0 |

TABLE 1-continued

Results of alkenylation reaction between ethylene and benzene

| | Catalyst | Formal oxidation state | Oxidizing agent | β-diketone | Molar concentration of product (mM) | | TDF ($\times 10^{-4} s^1$) | |
|---|---|---|---|---|---|---|---|---|
| | | | | | Vinyl acetate | Styrene | Vinyl acetate | Styrene |
| Comp. Example 2 | Rh(acac)(CO)$_2$ | Rh(I) | O$_2$ | — | 0.0 | 0.0 | 0.0 | 0.0 |
| Example 2 | Rh(NBD)(DPPB)BF$_4$ | Rh(I) | O$_2$ | acacH | 0.0 | 21.6 | 0.0 | 180.3 |
| Comp. Example 3 | Rh(NBD)(DPPB)BF$_4$ | Rh(I) | Cu(OAc)$_2$/O$_2$ | — | 4.1 | 4.1 | 34.0 | 34.3 |
| Comp. Example 4 | Rh(NBD)(DPPB)BF$_4$ | Rh(I) | O$_2$ | — | 0.0 | 1.6 | 0.0 | 13.0 |
| Comp. Example 5 | Pd(OAc)$_2$ | Pd(II) | O$_2$ | acacH | 14.5 | 57.9 | 121.2 | 482.2 |
| Comp. Example 6 | Pd(OAc)$_2$ | Pd(II) | Cu(OAc)$_2$/O$_2$ | — | 43.8 | 39.4 | 364.9 | 328.2 |
| Example 3 | Rh(acac) (ethylene)$_2$ | Rh(I) | O$_2$ | acacH | 0.0 | 22.0 | 0.0 | 183.3 |
| Example 4 | [Rh(COD)Cl]$_2$ | Rh(I) | O$_2$ | acacH | 0.0 | 21.0 | 0.0 | 175.0 |
| Example 5 | RhCl(PPh$_3$)$_3$ | Rh(I) | O$_2$ | acacH | 0.0 | 21.5 | 0.0 | 179.2 |
| Example 6 | [Rh(Cp*)Cl$_2$]$_2$ | Rh(III) | O$_2$ | acacH | 0.0 | 1.0 | 0.0 | 8.1 |
| Example 7 | Rh(ppy)$_2$(OAc) | Rh(III) | O$_2$ | acacH | 0.0 | 2.7 | 0.0 | 22.3 |
| Example 8 | Rh(acac)(CO)$_2$ | Rh(I) | O$_2$ | hmhd | 0.0 | 19.1 | 0.0 | 159.0 |
| Example 9 | Rh(acac)(CO)$_2$ | Rh(I) | O$_2$ | hfacacH | 0.0 | 0.5 | 0.0 | 4.0 |
| Example 10 | Rh(acac)(CO)$_2$ | Rh(I) | O$_2$ | aa-be | 0.0 | 2.0 | 0.0 | 16.9 | acacH: 2, 4-pentanedione (acetylacetone)
hmhd: 2,2,6,6,-tetramethyl-3,5-heptanedione
hfacacH: 1,1,1,5,5,5-hexafluoro-2,4-pentanedione (1,1,1,5,5,5-hexafluoroacetylacetone)
aa-tb: tert-butyl acetoacetate (acetoacetic acid t-butyl ester)

Example 11

The reaction was conducted by the very same operation as in Example 1, except that a Rh(acac)(CO)$_2$/ethylbenzene/acetic acid solution having the Rh concentration of 1 mM and the ethylbenzene concentration of 7.8 M was used in place of Rh(acac)(CO)$_2$/benzen/acetic acid solution having the Rh concentration of 1 mM and the benzen concentration of 10.6 M. The results are shown in Table 2.

Example 12

A Rh(acac)(CO)$_2$/benzene/methyl acrylate/acetic acid solution having the Rh concentration of 1 mM, the benzene concentration of 9.0 M and the methyl acrylate concentration of 1.0 M was prepared from Rh(acac)(CO)$_2$, benzene, acetic acid and methyl acrylate. 3 ml of the resulting solution, a stir bar coated with Teflon, and 0.2 g of acetylacetone were introduced in a glass inner cylinder, which was then introduced in a stainless steel autoclave. After the atmosphere in the autoclave was purged by nitrogen, methane was injected up to 1.55 MPa at room temperature and oxygen was injected up to 2.10 MPa, followed by heating with stirring at 180° C. for 20 minutes. After cooling, the liquid phase was analyzed by gas chromatography. The results are shown in Table 2.

As is apparent from Table 2, alkenylation of ethylbenzene due to ethylene and alkenylation of benzene due to methyl acrylate proceeds similarly to alkenylation of benzene due to ethylene.

According to the method of the present invention, which is characterized in that a rhodium complex is used as a catalyst in the presence of oxygen and β-diketone is added, it is made possible to selectively alkenylate an aromatic hydrocarbon with an olefin not necessarily with a redox agent such as copper-containing compound or silver-containing compound.

This technique makes it possible to attain the preparation of an alkenyl-substituted aromatic hydrocarbon, particularly styrene, at a high selectivity. The present invention has such excellent operation and effect that there is no complication in removing an oxidation catalyst because a redox agent is not necessarily required.

It will be further understood by those skilled in the art that the foregoing description is a preferred embodiment of the disclosed device and that various changes and modifications may be made in the invention without departing from the spirit and scope thereof.

What is claimed is:

1. A method of preparing an alkenyl-substituted aromatic hydrocarbon, which comprises alkenylating an aromatic

TABLE 2

Results of alkenylation reaction between various olefins and aromatic hydrocarbons

| | Olefin | Aromatic hydrocarbon | Product | Molar concentration of product (mM) | TDF ($\times 10^{-4} s^1$) |
|---|---|---|---|---|---|
| Example 11 | Ethylene | Ethylenzene | Ethyl vinyl benzene | 19.2 | 160.0 |
| Example 12 | Methyl acrylate | Benzene | Methyl cinnamate and 2-phenyl acrylic acid methyl ester | 2.3 | 19.3 | hydrocarbon with an olefin using β-diketone together with a rhodium complex catalyst in the presence of oxygen.

2. A method of preparing an alkenyl-substituted aromatic hydrocarbon, which comprises alkenylating an aromatic hydrocarbon with an olefin using β-diketone together with a rhodium complex catalyst in the presence of oxygen and in the absence of a redox agent.

3. The method according to claim 1, wherein the olefin is a substituted or non-substituted olefin having 2 to 20 carbon atoms and the aromatic hydrocarbon is a monocyclic or polycyclic aromatic hydrocarbon having 6 to 20 carbon atoms.

4. The method according to claim 1, wherein the β-diketone is β-diketone represented by the following scheme (1)

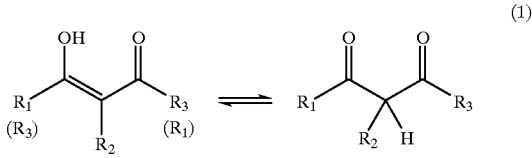

(1)

(provided that $R_1$ to $R_3$ respectively represent an arbitrary substituent and may be the same).

5. The method according to claim 2, wherein the β-diketone is β-diketone represented by the following scheme (1)

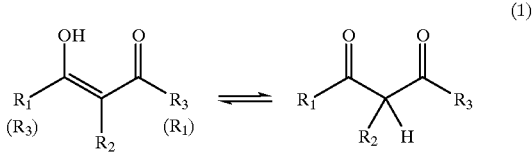

(1)

(provided that $R_1$ to $R_3$ respectively represent an arbitrary substituent and may be the same).

6. The method according to claim 1, wherein the diketone is 2,4-pentanedione(acetylacetone) or 2,2,6,6-tetramethyl-3,5-heptanedione.

7. The method according to claim 2, wherein the β-diketone is 2,4-pentanedione(acetylacetone) or 2,2,6,6-tetramethyl-3,5-heptanedione.

8. The method according to claim 1, wherein the rhodium complex is a complex in the formal oxidation state of Rh (I).

9. The method according to claim 2, wherein the rhodium complex is a complex in the formal oxidation state of Rh (I).

10. The method according to claim 1, wherein the rhodium complex is a complex having at least one rhodium atom and at least one β-diketonato ligand.

11. The method according to claim 2, wherein the rhodium complex is a complex having at least one rhodium atom and at least one β-diketonato ligand.

12. The method according to claim 1, wherein the rhodium complex is selected from the group consisting of dicarbonylacetylacetonatorhodium (I), acetylacetonatobis (ethylene)rhodium (I), chloro(1,5-cyclooctadiene)rhodium (I) dimer, chlorotris(triphenylphosphine)rhodium (I), and norbornadiene rhodium (I) tetrafluoroborate.

13. The method according to claim 2, wherein the rhodium complex is selected from the group consisting of dicarbonylacetylacetonatorhodium (I), acetylacetonatobis (ethylene)rhodium (I), chloro(1,5-cyclooctadiene)rhodium (I) dimer, cholorotris (triphenylphosphine) rhodium (I), and norbornadiene rhodium (I) tetrafluoroborate.

14. The method according to claim 12, wherein the olefin is ethylene and the aromatic hydrocarbon is benzene.

15. The method according to claim 13, wherein the olefin is ethylene and the aromatic hydrocarbon is benzene.

16. The method according to claim 1, wherein a molar ratio of the aromatic hydrocarbon to the rhodium complex is within a range from 100000:1 to 10:1.

17. The method according to claim 1, wherein a molar ratio of the aromatic hydrocarbon to the olefin compound is within a range from 0.1:1 to 1000:1.

18. The method according to claim 1, wherein a molar ratio of β-diketone to the rhodium complex catalyst the molar ratio is 1:1 or more.

19. The method according to claim 1, wherein the method is carried out at a reaction temperature within a range from room temperature to 300° C.

20. The method according to claim 1, wherein the method carried out at reaction pressure within a range from atmospheric pressure to 30 MPa.

21. A method of preparing an alkenyl-substituted aromatic hydrocarbon, which comprises alkenylating an aromatic hydrocarbon with an olefin using β-diketone together with a rhodium complex catalyst in the presence of oxygen, wherein the β-diketone is 2,4-pentanedione (acetylacetone) or 2,2,6,6-tetramethyl-3,5- heptanedione.

22. A method of preparing an alkenyl-substituted aromatic hydrocarbon, which comprises alkenylating an aromatic hydrocarbon with an olefin using β-diketone together with a rhodium complex catalyst in the presence of oxygen, wherein the rhodium complex is a complex having at least one rhodium atom and at least one β-diketonato ligand.

23. A method of preparing an alkenyl-substituted aromatic hydrocarbon, which comprises alkenylating an aromatic hydrocarbon with an olefin using β-diketone together with a rhodium complex catalyst in the presence of oxygen, wherein the rhodium complex is selected from the group consisting of dicarbonylacetylacetonatorhodium (I) dimer, chlorotris(triphenylphosphine)rhodium (I), and norbornadiene rhodium (I) tetrafluoroborate.

* * * * *